United States Patent [19]

Lai

[11] Patent Number: 4,942,894

[45] Date of Patent: Jul. 24, 1990

[54] MULTI PURPOSE CARTRIDGE TYPE HANDLE ASSEMBLY AND TOOLS

[76] Inventor: Ming-Der Lai, No. 53-2, Lane 239, Pa Der 3rd Road, Pan Chiau City, Taipei Hsien, Taiwan

[21] Appl. No.: 441,981

[22] Filed: Nov. 28, 1989

[51] Int. Cl.$^5$ .................... A61C 15/00; A61B 17/00
[52] U.S. Cl. .................... 132/323; 16/114 R; 81/487; 81/491; 30/334; 15/167.1; 15/176.1; 15/176.5
[58] Field of Search ............ 16/114 R; 81/177.1, 81/487, 489, 491; 15/145, 167.1, 172, 176.1; 132/323; 30/334

[56] References Cited

U.S. PATENT DOCUMENTS

| 1,175,275 | 3/1916 | Knauff et al. | 15/176.1 |
| 2,503,134 | 4/1950 | Schroeder | 15/176.1 |
| 3,174,174 | 3/1965 | Dengler | 15/176.1 |
| 4,051,857 | 10/1977 | Zambito | 132/323 |

FOREIGN PATENT DOCUMENTS 649074  8/1928  France .................... 15/172

Primary Examiner—Nicholas P. Godici
Assistant Examiner—Carmine Cuda
Attorney, Agent, or Firm—Karl W. Flocks

[57] ABSTRACT

"A multi-purpose cartridge type handle assembly" utilizing a movable block wedged in a "U"-shaped bracket and urged by a spring to hold various adaptors fitted with special sanitary tools for flexible operations.

2 Claims, 3 Drawing Sheets

MULTI PURPOSE CARTRIDGE TYPE HANDLE ASSEMBLY AND TOOLS

FIELD OF INVENTION

The present invention relates to a multi-purpose cartidge type handle assembly having adaptors fitted with various tools for flexible operations for personal cleaning purpose.

The multi-purpose cartridge type handle assembly, with its handle body, adaptors, and sanitary tools, enables a person to use it as tooth string, tooth brush, operation knife, etc.

Usually, the tooth brush and tooth string used to clean the dirt in crevices between teeth are separate and independent units. Its brush or string is fixed and does not work conveniently and can not clean the dirt completely either, and that is a common complaint by the users. With this point of view, the inventor has made intensive research to improve. After numerous tests and continuous improvements, a final design has developed. It not only corrects all past deficiencies, but also increases other functions of the handle for the users.

The construction of the handle assembly consists of the handle body and the tool adaptor. The handle body includes the body frame, a movable block wedged in the frame, and a spring installed between the handle head of the frame and the movable block; the body frame has a square handle head with a projected round tenon on one end to fix the spring and a "U"-shaped bracket fixed on both sides; the movable block is solid and rectangular, with also a projected round tenon on one end to fix the spring and a tongue on the other end having a concave bow-shaped edge, that presses the tool adaptor against the bottom loop of the U-shaped frame to hold the adaptor firmly; on both sides of the movable block, there is a long concave slot, of which the width is closely matched with the thickness of the U-shaped frame but allows the movable block to move along the frame; the sanitary tool can be a tooth string, tooth brush, or operation knife, which adaptor has a round pole with a bigger round head, or is of rectangular shape with a slot on both ends, pressed with spring pressure through the tongue of the block against the U-shaped frame to be held firmly.

Objects and features of the present invention are: firstly to provide an apparatus to hold a tooth brush or string for cleaning teeth, and the brush head can be turned by 360 degree which is very convenient to operate and able to clean the dirt in the crevice between teeth completely; secondly, when it is fitted with sanitary tools, it can be used as an ordinary tooth brush or operation knife; thirdly, this multi-purpose cartridge type handle assembly can be disassembled and assembled very easily for cleaning and sterilizing.

DETAILED DESCRIPTION OF THE INVENTION

Figure 1:
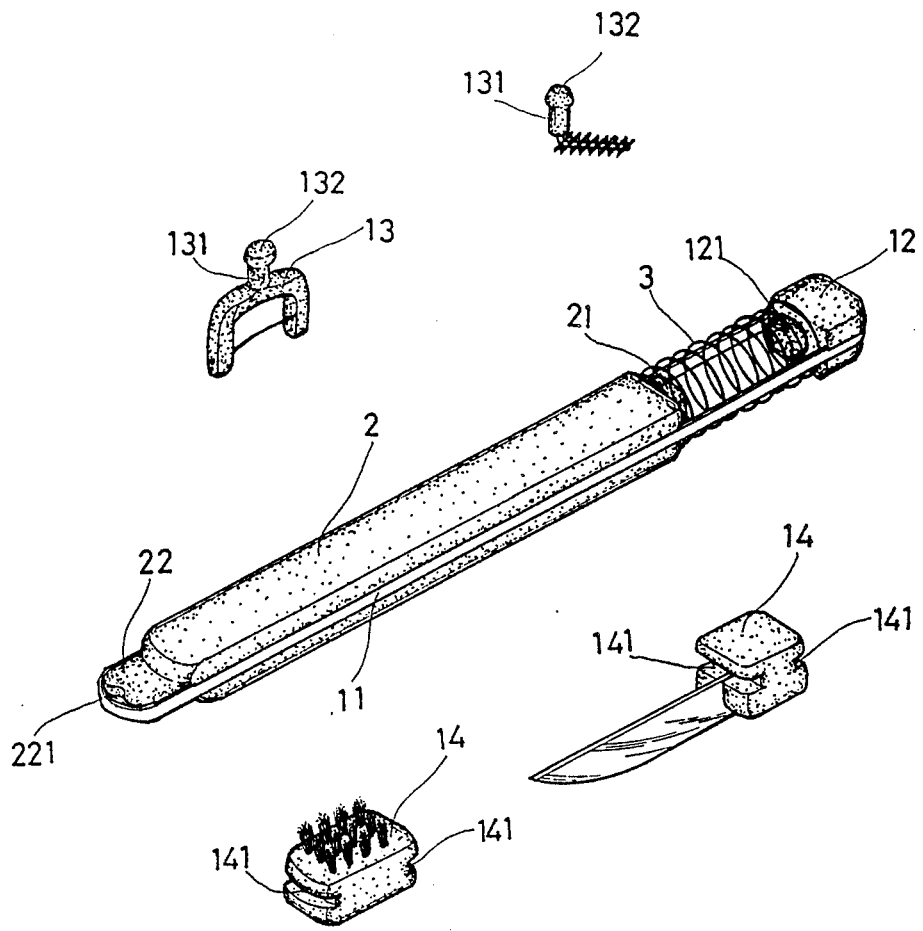
FIG. 1 is a perspective view of the handle assembly and various sanitary tool attachments.
Figure 2:
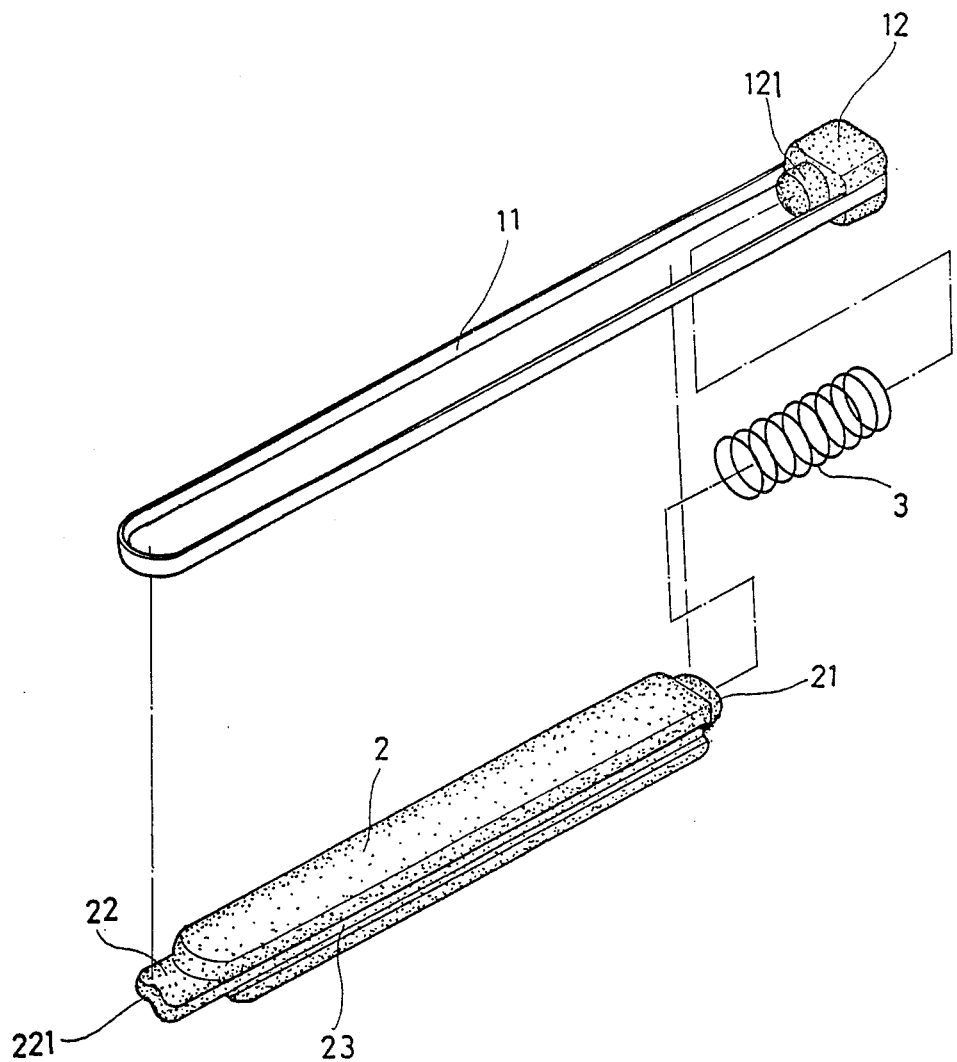
FIG. 2 is an exploded view of the handle body.

Referring first to FIGS. 1 and 2, the invention consists of the handle body and various attached sanitary tools; the handle body includes a body frame and a movable block 2, wedged in the frame, and the spring 3 pressingly located between the handle head 12 and a movable block 2. The handle body frame is composed of a square handle head 12 and a U-shaped bracket 11 with its two open ends fixed to the sides of the handle head 12. The handle head 12 has a round tenon 121 on one end to fix the spring 3; the movable block 2 is solid and rectangular and also has a round tenon 21 on one end to fix the spring 3, and a tongue 22 on the other end with a concave bow-shaped edge 221 which is urged by the spring 3 against the bottom loop of the body frame to hold the sanitary tool adaptor 13 or 14. The movable block 2 has concave slot 23 on both side, of which the width is closely matched with the thickness of the U-shaped bracket 11, but permitting the movable block 2 to move along the bracket 11. One end of the spring 3 is fitted over the round tenon 121 of the handle head 12 and its other end over the round tenon 21 of the movable block 2, so the spring 3 is extending and fixed between the handle head 12 and the movable block 2. The sanitary tool can be a tooth string, a tooth brush, or an operation knife, which is attachable to the handle body with an adaptor 13 or 14. The adaptor 13 has a small round pole 131 with a bigger round head 132, and the adaptor 14 is solid and rectangular with concave slot 141 on both sides and the tongue 22 on the end of movable block 2 pressed by the spring 3 sliding on the U-shaped bracket 11 to hold the adaptor 13 or 14 against the bottom loop of the U-shaped bracket. As shown in FIG. 2, it is very convenient to get the body frame 1 and the movable block 2 detached from the handle body for cleaning and sterilizing purposes.

Figure 3:
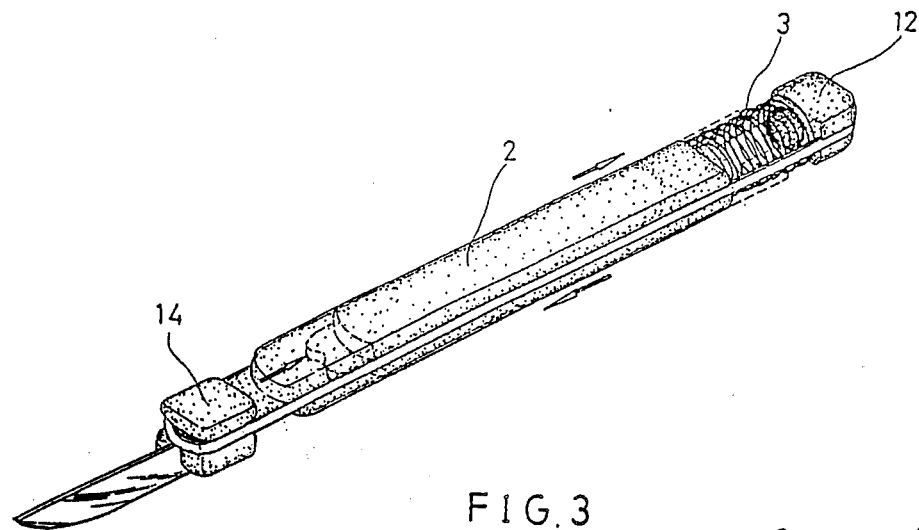
FIG. 3 is an assembly of the handle with an operation knife.
Figure 4:
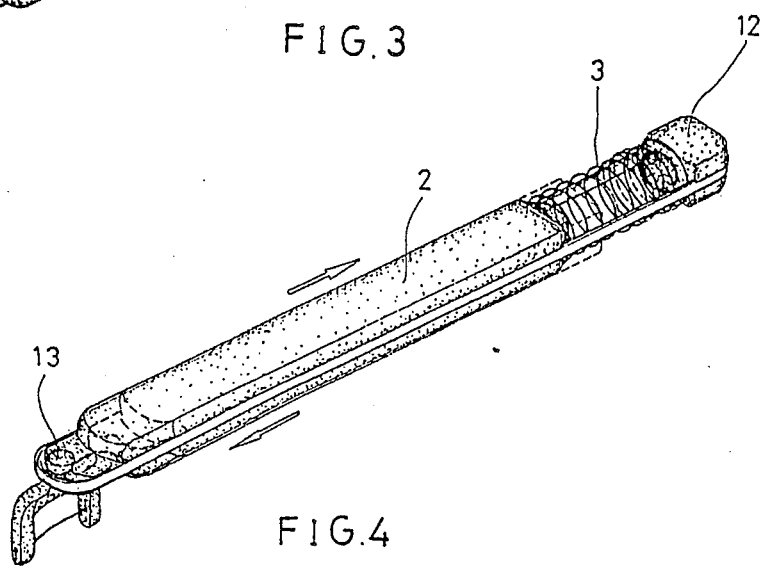
FIG. 4 is an assembly of the handle with a tooth string.

Referring to FIGS. 3 and 4, the use of the handle assembly is also very convenient. The operator only has to push back the movable block 2 against the pressure of the spring 3 between the movable block 2 and the handle head 12, and locate the adaptor 13 or 14 with the sanitary tool between the bottom loop of the U-shaped bracket and the tongue 22 of the movable block 2, then release the movable block 2, and the spring 3 urges it to hold the adaptor 13 or 14 and the handle assembly with a sanitary tool ready for use.

I claim:

1. A multi-purpose cartridge type handle assembly, including a handle body and sanitary tool adaptor means; the handle body being composed of a body frame, a movable block wedged in the body frame, and a spring fixed between a handle head of the body frame and said movable block; the handle body being able to be assembled and disassembled with ease; sanitary tools including a tooth brush for cleaning the crevice between teeth; a tooth string, and a brush head of common tooth brush, and an operation knife; the body frame comprising said handle head and a U-shaped bracket with both ends fixed to said handle head, said handle head having one round tenon; said movable block being solid and rectangular and having a round tenon on one end and a tongue with a concave bow-shaped edge on the other end; said movable block also having a long concave slot on both sides, of which the width is closely matched with the thickness of the U-shaped bracket, but permitting the movable block to slide along the bracket; the spring having one end fitted over the round tenon of said handle head and the other end fitted over the round tenon of said movable block.

2. A multi-purpose cartridge type handle assembly as mentioned in the claim 1, in which said sanitary tool adaptor means attached to the handle body frame is a small round pole with an enlarged round head at one end thereof, or a solid rectangular piece with a concave slot on both sides thereof.

* * * * *